United States Patent
Nousiainen et al.

(10) Patent No.: US 10,426,360 B2
(45) Date of Patent: Oct. 1, 2019

(54) PORTABLE PULSE MEASURING DEVICE

(71) Applicant: PULSEON OY, Espoo (FI)

(72) Inventors: Jari Nousiainen, Espoo (FI); Ilkka Korhonen, Lempaala (FI)

(73) Assignee: PULSEON OY, Espoo (FI)

( * ) Notice: Subject to any disclaimer, the term of this patent is extended or adjusted under 35 U.S.C. 154(b) by 960 days.

(21) Appl. No.: 14/891,357

(22) PCT Filed: May 15, 2014

(86) PCT No.: PCT/FI2014/050372
§ 371 (c)(1),
(2) Date: Nov. 15, 2015

(87) PCT Pub. No.: WO2014/184447
PCT Pub. Date: Nov. 20, 2014

(65) Prior Publication Data
US 2016/0081567 A1    Mar. 24, 2016

(30) Foreign Application Priority Data

May 15, 2013   (FI) ..................................... 20135520

(51) Int. Cl.
*A61B 5/024*        (2006.01)
*A61B 5/1455*     (2006.01)
(Continued)

(52) U.S. Cl.
CPC .......... *A61B 5/02433* (2013.01); *A61B 5/024* (2013.01); *A61B 5/0261* (2013.01);
(Continued)

(58) Field of Classification Search
None
See application file for complete search history.

(56) References Cited

U.S. PATENT DOCUMENTS

| 5,228,449 A | 7/1993 | Christ et al. |
| 5,431,170 A | 7/1995 | Mathews |

(Continued)

FOREIGN PATENT DOCUMENTS

| CN | 1929777 | 3/2007 |
| CN | 101108126 | 1/2008 |

(Continued)

OTHER PUBLICATIONS

Japanese Office Action for Japanese Application No. JP2016-513418, dated Apr. 3, 2018, 2 Pages.

(Continued)

*Primary Examiner* — Jason T Yen
(74) *Attorney, Agent, or Firm* — Brooks Kushman P.C.

(57) ABSTRACT

A portable pulse measuring device having a lighting configuration having at least three elements selected from a light-emitting source for emitting radiant energy through a human body tissue and a light detector for detecting the intensity of said radiant energy after propagation through the human body tissue and for providing input signals representative of the propagation. The lighting configuration includes at least one light-emitting source and at least one light detector. A processor is provided for determining pulse rate in response to processing the input signals. The elements in the lighting configuration are arranged in the portable pulse measuring device in a configuration where the light-emitting sources in the lighting configuration are asymmetrically disposed in relation to the light detectors in the lighting configuration.

16 Claims, 7 Drawing Sheets

(51) Int. Cl.
*A61B 5/00* (2006.01)
*A61B 5/026* (2006.01)
*A61B 5/0295* (2006.01)

(52) U.S. Cl.
CPC ........ *A61B 5/0295* (2013.01); *A61B 5/02416* (2013.01); *A61B 5/02427* (2013.01); *A61B 5/02438* (2013.01); *A61B 5/14551* (2013.01); *A61B 5/7203* (2013.01); *A61B 5/726* (2013.01); *A61B 5/7207* (2013.01); *A61B 5/7221* (2013.01); *A61B 2560/0209* (2013.01)

(56) References Cited

U.S. PATENT DOCUMENTS

| | | |
|---|---|---|
| 6,181,959 B1 | 1/2001 | Schollermann et al. |
| 7,162,228 B2 | 1/2007 | Bleile et al. |
| 7,372,778 B2 | 5/2008 | Klopfenstein et al. |
| 2002/0082489 A1* | 6/2002 | Casciani ............ A61B 5/14542 600/338 |
| 2003/0065269 A1* | 4/2003 | Vetter ................ A61B 5/02416 600/503 |
| 2004/0034294 A1* | 2/2004 | Kimball ............ A61B 5/02125 600/323 |
| 2005/0187446 A1 | 8/2005 | Nordstrom et al. |
| 2006/0211922 A1* | 9/2006 | Al-Ali ................ A61B 5/14552 600/310 |
| 2006/0224054 A1 | 10/2006 | Moriya et al. |
| 2006/0253010 A1 | 11/2006 | Brady et al. |
| 2009/0054571 A1 | 2/2009 | Ostroff et al. |
| 2009/0054751 A1 | 2/2009 | Babashan et al. |
| 2009/0326354 A1 | 12/2009 | Mao et al. |
| 2010/0056934 A1 | 3/2010 | Cho et al. |
| 2010/0113948 A1* | 5/2010 | Yang ................ A61B 5/02416 600/500 |
| 2010/0331638 A1 | 12/2010 | Besko |
| 2011/0112387 A1 | 5/2011 | Li et al. |
| 2012/0022382 A1* | 1/2012 | Daisuke ................ A61B 5/002 600/481 |
| 2012/0172684 A1 | 7/2012 | Buchheim et al. |
| 2013/0261415 A1 | 10/2013 | Ashe et al. |

FOREIGN PATENT DOCUMENTS

| | | |
|---|---|---|
| EP | 1297784 | 4/2003 |
| EP | 1886624 | 2/2008 |
| JP | 2003508144 | 3/2003 |
| WO | 9403102 | 2/1994 |
| WO | 0117421 | 3/2001 |
| WO | 2007012931 | 2/2007 |
| WO | 2007097702 | 8/2007 |
| WO | 2012110955 | 8/2012 |

OTHER PUBLICATIONS

Extended European Search Report for European Application No. EP 14798224.3, Completed by the European Patent Office, dated Jan. 18, 2017, 9 Pages.
Chinese Search Report for Chinese Application No. CN 2014800277262, Completed by the Chinese Patent Office, dated Jan. 23, 2017, 2 Pages.
Chinese Office Action for Chinese Application No. CN 201480027726. 2, English translation attached to original, Both completed by the Chinese Patent Office, dated Feb. 4, 2017, All together 13 Pages.
International Search Report for PCT/FI2014/050372, Completed by the Finnish Patent Office dated Aug. 20, 2014, 8 Pages.
Finnish Search Report for App No. 20135520, Completed by the Finnish Patent Office, dated Sep. 9, 2015, 8 Pages.

\* cited by examiner

PORTABLE PULSE MEASURING DEVICE

CROSS-REFERENCE TO RELATED APPLICATION

This application is the U.S. national phase of PCT Application No. PCT/FI2014/050372 filed on May 15, 2014, which claims priority to FI Patent Application No. 20135520 filed on May 15, 2013, the disclosures of which are incorporated in their entirety by reference herein.

TECHNICAL FIELD

The present invention relates to pulse measuring devices.

BACKGROUND

Various pulse rate detection systems are known in the art. The pulse rate detection devices comprise, for example, devices that use pressure sensitive transducers such as piezoelectric elements to detect pulse rate.

Another measuring technique is called as photoplethysmography. Photoplethysmography is an electro-optic technique of measuring the cardiovascular pulse wave found throughout the human body. The pulse wave is caused by the periodic pulsations of arterial blood volume and is measured by the changing optical absorption of radiant energy which this induces.

The measurement system usually consists of a source of radiant energy (for example, an infra-red light source), at least one detector for detecting the intensity of the radiant energy after propagation through the human body tissue and a data processing means for extracting bodily parameters such as pulse rate or oxygen concentration in the blood. For example, the use of infra-red light has certain advantages. It is relatively little absorbed in blood and in body tissue and blood volume changes are therefore observed with a reasonable contrast with relatively low radiant energy. The use of other light wavelengths is also possible. The use of photoplethysmography as a measuring technique is entirely non-invasive and can be applied to any blood bearing tissue, for example, a finger, nail, ear lobe, nose and wrist.

The light intensity varies together with changes in the volume in the tissue of interest both due to changes in the path-length between the light-source and the photo detector (due to volume changes) and due to the changes in the optical density of the tissue including blood and liquids (e.g. due to arterial blood pulsation). In a homogeneous layer of blood, the Beer-Lambert law suggests light intensity to decay exponentially as a function of distance due to light absorption. However, no tissue is homogeneous, and hence in addition to light absorption factors such as light scatter, refraction and reflection, which all depend on the exact anatomy and geometry of the tissue, also affect the measured signal. Therefore, the total amount of radiant energy reaching detector is sensitive to sensor positioning and any deformations of the tissue.

It is characteristic to a human tissue that light is highly scattered in the tissue. Therefore, a detector positioned on the surface of the skin is able to measure reflections. These reflections are variously absorbed depending on whether the light encounters weakly or highly absorbing tissue. Any change in blood volume will be registered by the detector at the surface since increasing (or decreasing) volume will cause more (or less) absorption. When the illuminated blood flow pulsates, it alters mainly the total absorption coefficient of the tissue volume but also the optical path length and therefore modulates the light absorption throughout the cardiac cycle. Non-pulsating fluids and tissues do not modulate the light but have a constant level of absorption (assuming there is no movement or other deformation of the tissue volume).

The result of the absorption is that any light reflected from the pulsating vascular bed contains an AC component which is proportional to and synchronous with the subject's heart pumping action. It is this modulated component which is known as the photoplethysmographic signal. A plethysmographic measurement can be achieved by measurement of the intensity of radiant energy transmitted through (transmission mode systems) or reflected by (reflection mode systems) body tissue.

In theory, measuring a pulse rate is a simple measurement—at least one detector detects the intensity of the radiant energy received via human tissue and a data processing means is used to determine needed parameters from the signals received from the at least one detector. In practice, the situation is not so simple especially when the subject is moving. Movements cause deformation of the tissue volume between radiant energy source and detector which will cause changes which are not related to a heart pumping action in the detected energy in the detector. These movement artifacts may be typically manifold as compared to changes in the absorption caused by blood flow changes, and therefore complex methods have been proposed to compensate for these artifacts by processing means. One possible compensation solution is presented in EP 1 297 784 A1.

In the light of the present art, it is beneficial to minimize the amount of movement artifacts in the signal and to keep the proportion of the signal related to blood flow maximal. This may be achieved by arranging the measurement so that the tissue volume through which the radiant energy propagates before reaching the detector contains maximal relative proportion of active blood flowing vasculature, and only minimal amount of other tissue volume i.e. tissues in which blood pulsation is less significant. However, this has some complications.

First, thickness of skin and other layers of human tissue e.g. epidermis, papillary dermis and reticular dermis, varies between individuals and also between different spatial locations in the skin, and therefore the active blood containing tissue thickness and depth from skin surface is different in different individuals and/or spatial locations on skin. Furthermore, blood flow in different layers of the skin varies dynamically between different conditions so that when skin is cold blood circulation is minimal close to skin surface while with warm skin blood flow is active close to skin surface. These aspects make it challenging to provide a reliable measurement.

In addition, portable pulse rate measuring device should optimally have a small size and long battery life to be most useful for their users.

Based on the above, there is a need for solution that would take into account at least some of the above aspects and variances that affect to pulse rate measurements and that would provide a reliable pulse rate measurement.

SUMMARY

According to an aspect of the invention, there is provided a portable pulse measuring device. The device comprises a lighting configuration comprising at least three elements selected from a light-emitting source for emitting radiant energy through a human body tissue and a light detector for detecting the intensity of said radiant energy after propagation through the human body tissue and for providing input signals representative of said propagation, wherein the lighting configuration comprises at least one light-emitting source and at least one light detector; processing means configured to determine pulse rate in response to processing the input signals. The elements in the lighting configuration are arranged in the portable pulse measuring device in a configuration where the light-emitting sources in the lighting configuration are asymmetrically disposed in relation to the light detectors in the lighting configuration.

In one embodiment the light-emitting sources in the lighting configuration are arranged such that the distances from the light-emitting sources to the light detectors in the lighting configuration differ from each other.

In one embodiment the lighting configuration comprises at least two light-emitting sources emitting the same wavelength.

In one embodiment the lighting configuration comprises at least two light-emitting sources emitting at least two different wavelengths.

In one embodiment the lighting configuration comprises two light detectors and two light-emitting sources comprising a first light-emitting source and a second light-emitting source wherein the first and second light-emitting sources emit different wavelengths. In one embodiment the two light detectors and the first light-emitting source are disposed along a first axis, the first light-emitting source being disposed between the two light detectors on the first axis, and the first light-emitting source and the second light-emitting source are disposed along a second axis. In one embodiment the distances from the first light-emitting source to the two light detectors differ from each other and the distances from the second light-emitting source to the two light detectors differ from each other. In one embodiment the distances from the first light-emitting source to the two light detectors and the distances from the second light-emitting source to the two light detectors are chosen to provide an optimal measurement range in the human body tissue.

In one embodiment the device further comprises blocking means for blocking direct light leakage from the at least two light-emitting sources to the at least one light detector.

In one embodiment the first light-emitting source is configured to emit shorter wavelength visible light and the second light-emitting source is configured to emit longer wavelength visible light.

In one embodiment the shorter wavelength visible light comprises green or blue light and the longer wavelength visible light comprises infrared or red light In one embodiment the processing means are configured to determine whether a channel comprising a specific light detector detecting radiant energy from a specific light-emitting source exceeds a first reliability factor threshold, the reliability factor indicating an estimate of the reliability of the heart rate reading for each channel, and to select a channel having a reliability factor above the first reliability factor threshold.

In one embodiment the processing means are configured to select a channel having the highest reliability factor. In another embodiment, the processing means are configured to select a channel having the lowest power consumption.

In one embodiment the processing means are configured to shut operating power from at least one other channel not selected.

In one embodiment the processing means are configured to reduce light intensity of the light-emitting source of the selected channel so that the reliability factor of the selected channel exceeds the first reliability factor threshold.

In one embodiment the processing means are configured to increase light intensity of the light-emitting source of the selected channel so that the reliability factor of the selected channel exceeds the first reliability factor threshold.

In one embodiment the processing means are configured to determine that the reliability factor of a channel is below the first reliability factor threshold; power on at least one channel the operating power of which was earlier shut down; determine the reliability factor again for each channel; and reselect a channel having the reliability factor above the first reliability factor threshold, or having the reliability factor above the first reliability factor threshold and the lowest power consumption.

In one embodiment the processing means are configured to determine that the reliability factor of a channel is below a second reliability factor threshold and to shut down operating power from the channel.

In one embodiment the reliability factor is calculated as $SNR=\|X_{HR}\|/\|X_{nHR}\|$, where $X_{HR}$ is the ratio of the signal related to pulsative blood flow, XnHR is the ratio of the signal not related to pulsatile blood flow, and $\|\cdot\|$ is a signal norm operator. In one embodiment $\|\cdot\|$ is a signal power operator or a signal amplitude operator. It is clear to a person skilled in the art that several other possible norm operators may also be used.

According to another aspect of the invention, there is provided a portable pulse measuring device, comprising: a lighting configuration comprising at least two light-emitting sources for emitting radiant energy through a human body tissue and at least one light detector for detecting the intensity of said radiant energy after propagation through the human body tissue and for providing input signals representative of said propagation, wherein the at least two light-emitting sources comprise a first light-emitting source emitting a first wavelength and a second light-emitting source emitting a second wavelength for determining pulse rate; processing means configured to determine pulse rate in response to processing the input signals; wherein the elements in the lighting configuration are arranged in the portable pulse measuring device in a configuration where the distance from the first light-emitting source to a first light detector and the distance from the second light-emitting source to the first light detector differ from each other; and wherein the distances from the first and second light-emitting sources to the first light detector and the first and second wavelengths have been chosen to enable measurement of a variety of measurement depths in the human body tissue and to provide sensitivity to blood flow and insensitivity against to movement artefacts in varying conditions.

In one embodiment, the lighting configuration comprises at least two light-emitting sources emitting the same wavelength In one embodiment, the lighting configuration comprises three light-emitting sources and the first light detector, wherein two light-emitting sources are arranged at equal distances from the first light detector and on opposite sides of the first light detector substantially on the same axis, and wherein the two light-emitting sources emit the first wavelength and the third light-emitting source emits the second wavelength and wherein the distance from the two light-emitting sources to the first light detector and the distance from the third light-emitting source to the first light detector differ from each other.

In one embodiment, the first light-emitting source emits green light and the second light-emitting source emits infrared light, and the distance between the center of the first light detector and the first light-emitting source is between 2.5 mm and 4.5 mm and preferable about 3.6 mm, and the distance between the center of the first light detector and the second light-emitting source is between 4.0 mm and 7.0 mm and preferably about 6.0 mm.

In one embodiment, the lighting configuration comprises two light detectors and wherein the first light detector and a second light detector and the first light-emitting source are disposed substantially along a first axis, the first light-emitting source being disposed between the first and second light detectors, and the first light-emitting source and the second light-emitting source are disposed along a second axis differing from the first axis.

In one embodiment, the distances from the first light-emitting source to the two light detectors differ from each other and the distances from the second light-emitting source to the two light detectors differ from each other. In one embodiment, the first light-emitting source emits green light and the second light-emitting source emits infrared light, wherein distance between the center of the first light detector and the first light-emitting source is between 2.0 mm and 4.0 mm and preferably about 3.0 mm, the distance between the center of the second light detector and the first light-emitting source is between 4.0 mm and 6.0 mm and preferably about 5.0 mm, the distance between the center of the first light detector and the second light-emitting source is between 4.0 mm and 6.0 mm and preferably about 5.0 mm, and the distance between the center of the second light detector and the second light-emitting source is between 6.5 mm and 8.5 mm and preferably about 7.5 mm.

In one embodiment, the device further comprises blocking means for blocking direct light leakage from the at least two light-emitting sources to the at least one light detector.

In one embodiment, the first light-emitting source is configured to emit shorter wavelength visible light and the second light-emitting source is configured to emit light having longer wavelength than the shorter wavelength visible light.

In one embodiment, the shorter wavelength visible light comprises green or blue light and the longer wavelength light comprises infrared or red light.

In one embodiment, the processing means are configured to: determine whether a channel comprising a specific light detector detecting radiant energy from a specific light-emitting source exceeds a first reliability factor threshold, the reliability factor indicating an estimate of the reliability of the heart rate reading for the channel; and select a channel having a reliability factor above the first reliability factor threshold.

In one embodiment, the processing means are configured to select a channel having the highest reliability factor.

In one embodiment, the processing means are configured to select a channel having the lowest power consumption.

In one embodiment, the processing means are configured to shut operating power from at least one channel not selected.

In one embodiment, the processing means are configured to reduce light intensity of the light-emitting source of the selected channel so that the reliability factor of the selected channel exceeds the first reliability factor threshold.

In one embodiment, the processing means are configured to increase light intensity of the light-emitting source of the selected channel so that the reliability factor of the selected channel exceeds the first reliability factor threshold.

In one embodiment, the processing means are configured to: determine that the reliability factor of a channel is below the first reliability factor threshold; power on at least one channel the operating power of which was earlier shut down; determine the reliability factor again for one or more channels; and reselect a channel having the reliability factor above the first reliability factor threshold, or having the reliability factor above the first reliability factor threshold and the lowest power consumption.

In one embodiment, the processing means are configured to: determine that the reliability factor of a channel is below a second reliability factor threshold; and shut down operating power from the channel.

In one embodiment, the reliability factor is calculated as $SNR=\|X_{HR}\|/\|X_{nHR}\|$, where $X_{HR}$ is the portion of the signal related to pulsative blood flow, $X_{nHR}$ is the portion of the signal not related to pulsatile blood flow, and $\|\cdot\|$ is a signal norm operator.

According to another aspect of the invention, there is provided a method for processing input signals of a portable pulse measuring device of any of the aspects above. The method comprises determining whether a channel comprising a specific light detector detecting radiant energy from a specific light-emitting source exceeds a first reliability factor threshold, the reliability factor indicating an estimate of the reliability of the heart rate reading for each channel; and selecting a channel having a reliability factor above the first reliability factor threshold.

In one embodiment the method comprises selecting a channel having the highest reliability factor.

In one embodiment the method comprises selecting a channel having the lowest power consumption.

In one embodiment the method comprises shutting operating power from at least one channel not selected.

In one embodiment the method comprises reducing light intensity of the light-emitting source of the selected channel so that the reliability factor of the selected channel exceeds the first reliability factor threshold.

In one embodiment the method comprises increasing light intensity of the light-emitting source of the selected channel so that the reliability factor of the selected channel exceeds the first reliability factor threshold.

In one embodiment the method comprises determining that the reliability factor of a channel is below the first reliability factor threshold; powering on at least one channel the operating power of which was earlier shut down; determining the reliability factor again for each channel; and reselecting a channel having the reliability factor above the first reliability factor threshold, or having the reliability factor above the first reliability factor threshold and the lowest power consumption.

In one embodiment the method comprises determining that the reliability factor of a channel is below a second reliability factor threshold; and shut down operating power from the channel.

According to another aspect of the invention, there is provided a computer program comprising program code, which when executed on a processor, executes the above method. The computer program may be embodied on a computer-readable medium.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION

Reference will now be made in detail to the embodiments of the present invention, examples of which are illustrated in the accompanying drawings.

Figure 1A:
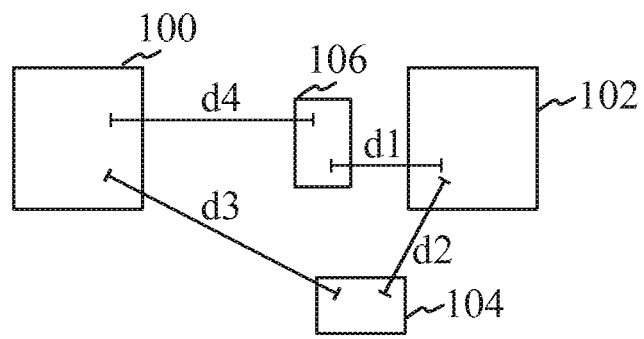
FIG. 1A is a block diagram illustrating an embodiment of a measurement arrangement in a portable measurement device in accordance with the present invention.

FIG. 1A is a block diagram illustrating an embodiment of a measurement arrangement in a portable measurement device in accordance with the present invention. The measurement arrangement disclosed in FIG. 1A comprises a first light detector 100 and a second light detector 102. The light detectors are, for example, photo detectors that are able to detect reflected light. The measurement arrangement also comprises two light-emitting sources 104, 106. In one embodiment, the measurement arrangement has been arranged onto a bottom side of a portable measurement device, which is carried, for example, on a wrist or some other part of the body, where the device is firmly touching the skin.

Tissue, for example, skin is illuminated by a light source, for example a light emitting diode (LED). In the arrangement of FIG. 1A, the first light-emitting source 104 emits infrared light and the second light-emitting source 106 emits green light. An optical signal is a signal derived as a variation of light intensity detected in the light detectors 100, 102 as a function of changes in light absorption in the tissue. Changes in light intensity may be caused by deformation of the tissue, for example, due to movements, or by changes in blood volume in the area, caused by pulsative blood flow. The latter is used for detection of heart rate.

The skin of the human tissue comprises several layers including epidermis, papillary dermis, reticular dermis and hypodermis. Skin properties also vary between individuals and anatomical location. Papillary dermis includes small vasculature which constrict when cold. Reticular dermis includes larger vasculature which are less sensitive to cold. The desired measuring depth where blood is to be measured occurs in epidermis which is usually about 0.6-3 mm deep. Next tissue layer is mostly fat tissue and add artefacts to the detected signal if a significant portion of light is reflected from this tissue as fat tissue is sensitive to deformations caused by movements and contains no significant vasculature.

Tissue deformation due to movement causes major changes in light reflection paths within the tissue, leading to major changes in light intensity observed in the light detectors when the tissue is illuminated with constant light intensity. This relationship is dependent on the tissue volume through which the light travels, i.e. the higher the volume the more changes are caused by movements. Therefore, it is preferable to minimize tissue volume to be illuminated to minimize artifacts in the detected signals by the light detectors.

In reflectance photoplethysmography the penetration depth of the light to the tissue is mostly dependent on two factors:

1) The distance between the light detectors 100, 102 and the light-emitting sources 104, 106. The average penetration depth of the light in a homogenous tissue is roughly d/2 where d is the distance between a light detector and a light-emitting source.

2) Light wavelength affects light absorption in the tissue so that the shorter wavelengths (for example, green or blue) are absorbed significantly more than longer wavelengths, such as infrared and red. An absorption co-efficient for green light may be more than 10 times or even 100 times higher than for infrared or red light. For similar light level at a light detector, 10 times higher light intensity is needed.

Therefore, in accordance with the measurement arrangement disclosed in FIG. 1A, light penetration depth may be controlled by varying the distance d. In another embodiment, in addition to varying the distance d, also light wavelengths may be varied. For shallow penetration, small d and shorter wavelengths may be used while larger d and longer wavelengths may be used for deeper penetration. By varying the distance d or both factors (distance d and used wavelengths) independently, it is possible to optimize the penetration depth better in a non-homogeneous tissue.

In the embodiment of FIG. 1A, the first light-emitting source 104 emits infrared light and the second light-emitting source 106 emits green light. Further, the distance d1 is about 2.5 mm, the distance d2 is about 4 mm, the distance d3 is about 6 mm and the distance d4 is about 4 mm. Thus, the light-emitting sources 104, 106 are asymmetrically disposed in relation to the light detectors 100, 102. Although the embodiment of FIG. 1A specifically discloses the use of green and infrared light, other suitable wavelengths may also be used, for example, blue light and red light etc. The centres of the light detectors 100 and 102 and the light-emitting source 106 may be disposed substantially along a single axis. In another embodiment, the center point of the light-emitting source 106 may be below or above the axis determined by the centers of the light detectors 100 and 102.

The measurement arrangement disclosed in FIG. 1A provides a solution which enables measuring pulse rate from various tissue depths. In other words, a measurement depth can be used which provides the best detection result for the heart rate. The measurement arrangement disclosed in FIG. 1A also provides the possibility of varying the measurement depth in real-time or near real-time because it provides four different measurement channels (combinations of a light-emitting source and a light detector) to choose. For example, in cold skin conditions minimal blood flow occurs close to skin. Therefore deeper measurement may be applied. In warm skin conditions blood flow is active close to skin and therefore smaller measurement depth may be applied.

Furthermore, when tissue is illuminated with light through skin, absorption of light is caused by skin, blood containing tissue, and fat tissue (absorption similar to water). In total, absorption co-efficient for, for example, green light may be more than 10 times or even 100 times higher than that for infrared or red. As a result, green light attenuates rapidly in tissue and only very small volume of tissue is affecting light intensity as measured with a photo detector which is close to the light source. Therefore, green light is a good choice in situations where blood perfusion close to skin surface is good and movement artefacts (which are dependent on tissue volume deformation due to movement) need to be minimized. This is typical for example during physical exercise. However, due to high absorption co-efficient, required light intensity is higher with green light than for infrared light to gain similar average light intensity in a light detector, and therefore power consumption of the green light emitting light source is higher than that for infrared light source. Therefore, in situations where blood perfusion is deeper in tissue but not in the surface and/or when movement artefacts are small enough to gain sufficient signal quality infrared may be favored to save battery power and/or gain better signal quality. Furthermore, the human tissue in practice is not homogenous. Thus a significant amount of emitted light may reach the tissue layer comprising mainly fat causing undesired reflections. The use of green light minimizes this effect because green light does not reflect back well through the epidermis.

In one embodiment of FIG. 1A the light-emitting source 106 emits green light and the light-emitting source 104 emits infrared light. The distance d1 between the center of the light detector 102 and the light-emitting source 106 is between 2.0 mm and 4.0 mm and the distance d4 between the center of the light detector 100 and the light-emitting source 106 is between 4.0 mm and 6.0 mm. The distance d2 between the center of the light detector 102 and the light-emitting source 104 is between 4.0 mm and 6.0 mm and the distance d3 between the center of the light detector 100 and the light-emitting source 104 is between 6.5 mm and 8.5 mm. In a further embodiment the distance d1 between the center of the light detector 102 and the light-emitting source 106 is about 3.0 mm and the distance d4 between the center of the light detector 100 and the light-emitting source 106 is about 5.0 mm. The distance d2 between the center of the light detector 102 and the light-emitting source 104 is about 5.2 mm and the distance d3 between the center of the light detector 100 and the light-emitting source 104 is about 7.5 mm.

Figure 1B:
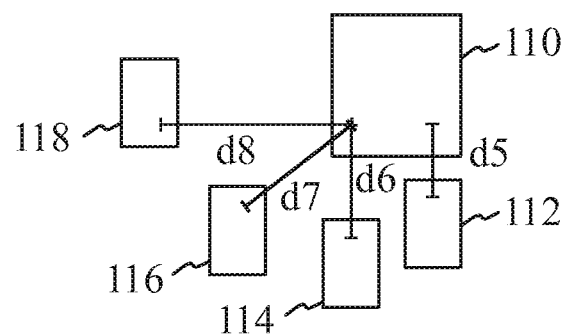
FIG. 1B is a block diagram illustrating another embodiment of a measurement arrangement in a portable measurement device in accordance with the present invention.

FIG. 1B is a block diagram illustrating another embodiment of a measurement arrangement in a portable measurement device in accordance with the present invention. Whereas FIG. 1A disclosed a pair of light detectors and a pair of light-emitting sources, FIG. 1B discloses only one light detector 110. Multiple light-emitting sources 112, 114, 116, 118 have been arranged around the light detector 110 where the distances d5, d6, d7, d8 from the light-emitting sources 112, 114, 116, 118 differ from each other. Thus, the light-emitting sources 112, 114, 116, 118 are asymmetrically disposed in relation to the light detector 110. The amount of light-emitting sources may also be more than disclosed in FIG. 1B or less than disclosed in FIG. 1B. The light-emitting sources 112, 114, 116, 118 may all transmit the same wavelength, for example red, infrared, blue or green light. In another embodiment the light-emitting sources 112, 114, 116, 118 include light-emitting sources which emit at least two different wavelengths.

Figure 1C:
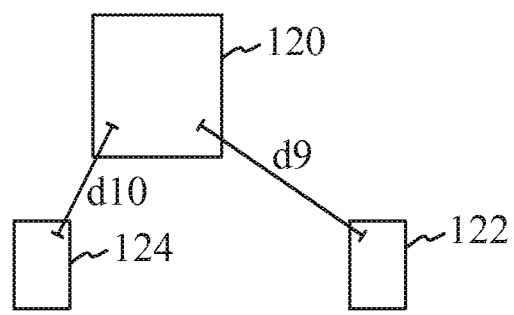
FIG. 1C is a block diagram illustrating another embodiment of a measurement arrangement in a portable measurement device in accordance with the present invention.

FIG. 1C is a block diagram illustrating another embodiment of a measurement arrangement in a portable measurement device in accordance with the present invention. The arrangement comprises one light detector 120 and two light-emitting sources 122, 124. The distances d9 and d10 from the light-emitting sources 122, 124 to the light detector 120 differ from each other. Thus, the light-emitting sources 122, 124 are asymmetrically disposed in relation to the light detector 120. In one embodiment of FIG. 1C the light-emitting source 124 emits green light and the light-emitting source 122 emits infrared light, and the distance d10 between the center of the light detector 120 and the light-emitting source 124 is between 2.5 mm and 4.5 mm and the distance d9 between the center of the light detector 120 and the light-emitting source 122 is between 4.0 mm and 7.0 mm. In a further embodiment the distance d10 between the center of the light detector 120 and the light-emitting source 124 is about 3.6 mm and the distance d9 between the center of the light detector 120 and the light-emitting source 122 is about 6.0 mm.

Figure 1D:
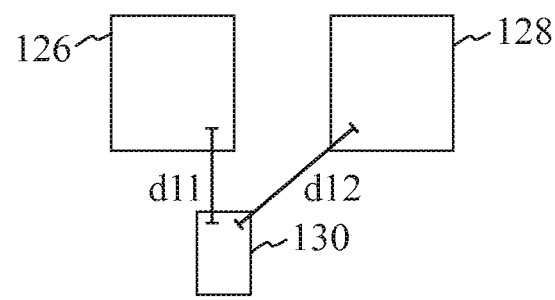
FIG. 1D is a block diagram illustrating another embodiment of a measurement arrangement in a portable measurement device in accordance with the present invention.
Figure 1E:
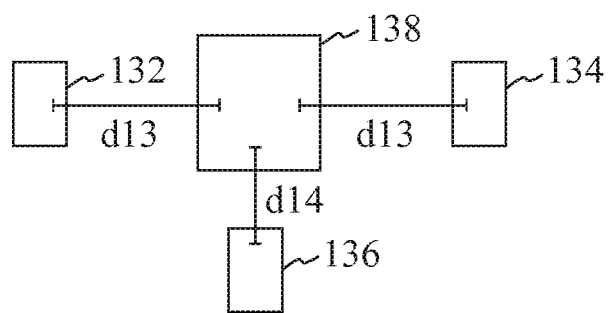
FIG. 1E is a block diagram illustrating another embodiment of a measurement arrangement in a portable measurement device in accordance with the present invention.

FIG. 1D is a block diagram illustrating another embodiment of a measurement arrangement in a portable measurement device in accordance with the present invention. The arrangement comprises two light detectors 126, 128 and a light-emitting source 130. The distances d11 and d12 from the light-emitting source 130 to the two light detectors 126, 128 differ from each other. Thus, the light-emitting source 130 is asymmetrically disposed in relation to the light detectors 126, 128. FIG. 1E is a block diagram illustrating another embodiment of a measurement arrangement in a portable measurement device in accordance with the present invention. The arrangement comprises a light detector 138 and three light-emitting sources 132, 134 and 136. The distances d13 from the light-emitting sources 132 and 134 to the light detector 138 are identical or substantially identical. The distance d14 from the light-emitting source 136 to the light detector 138 differs from the distance d13. In this embodiment, the light-emitting sources 132 and 134 are arranged to emit a first wavelength and the light-emitting source 136 is arranged to emit a second wavelength. In operation when measuring pulse with the light-emitting sources 132 and 134, the sources are powered on and off simultaneously. This makes it possible to cover a larger area with the light detector 138 than only with a single light-emitting source. In one embodiment, the light-emitting sources 132 and 134 emit green light and the light-emitting source 136 emits infrared light.

Further, when using the light-emitting sources 132, 134 and 136 in measuring pulse, the sources are powered on and off successively. In other words, the light-emitting sources 132 and 134 are powered on and off simultaneously while the light-emitting source 136 is powered on only after the light-emitting sources 132 and 134 have been powered off. This makes it possible to cover selectively a variety of measurement depths with the light detector 138 than only with a single light-emitting source and/or if only a single wavelength was used.

In one embodiment of FIG. 1E the light-emitting sources 132, 134 emit green light and the light-emitting source 136 emits infrared light, and the distance d13 between the center of the light detector 138 and the light-emitting sources 132, 134 is between 2.5 mm and 4.5 mm and the distance d14 between the center of the light detector 138 and the light-emitting source 136 is between 4.0 mm and 7.0 mm. In a further embodiment the distance d13 between the center of the light detector 138 and the light-emitting sources 132, 134 is about 3.6 mm and the distance d14 between the center of the light detector 138 and the light-emitting source 136 is about 6.0 mm.

FIGS. 1A, 1B, 1C, 1D and 1E disclose five specific measurement configurations. In other embodiments of the invention, the measurement configuration may be different as long as a lighting configuration comprises at least three elements selected from a light-emitting source for emitting radiant energy through a human body tissue and a light detector for detecting the intensity of said radiant energy after propagation through the human body tissue and for providing input signals representative of said propagation, wherein the lighting configuration comprises at least one light-emitting source and at least one light detector, wherein the elements in the lighting configuration are arranged in a configuration where the light-emitting sources in the lighting configuration are asymmetrically disposed in relation to the light detectors in the lighting configuration. In other words, light penetration depth to the human body tissue may be controlled by varying at least one distance d. In a further embodiment, also light wavelengths in addition to varying the distance may be varied by using light-emitting sources that emit different wavelengths.

The distances d1-d13 disclosed in FIGS. 1A-1E are preferably measured between centers of the disclosed elements.

In one embodiment of FIG. 1A, 1B, 1C, 1D or FIG. 1E, some means for blocking direct light leakage from the at least two light-emitting sources to the at least one light detector. This provides the advantage that the detection of the reflected light from the human tissue is not affected by light leakages from the light-emitting sources. The blocking means refer, for example, to any material or constructions that prevents direct light leakage from the at least two light-emitting sources to the at least one light detector.

At least one of the embodiments of FIG. 1A, 1B, 1C, 1D or FIG. 1E, the solution provides an ability to dynamically choose the active measurement depth i.e. the average depth through which the radiant energy reaches when passing from radiant energy source to the detector so that the tissue volume between the radiant energy source and detector would be maximally proportionate to blood flow and minimally sensitive to other tissue deformations.

Figure 2A:
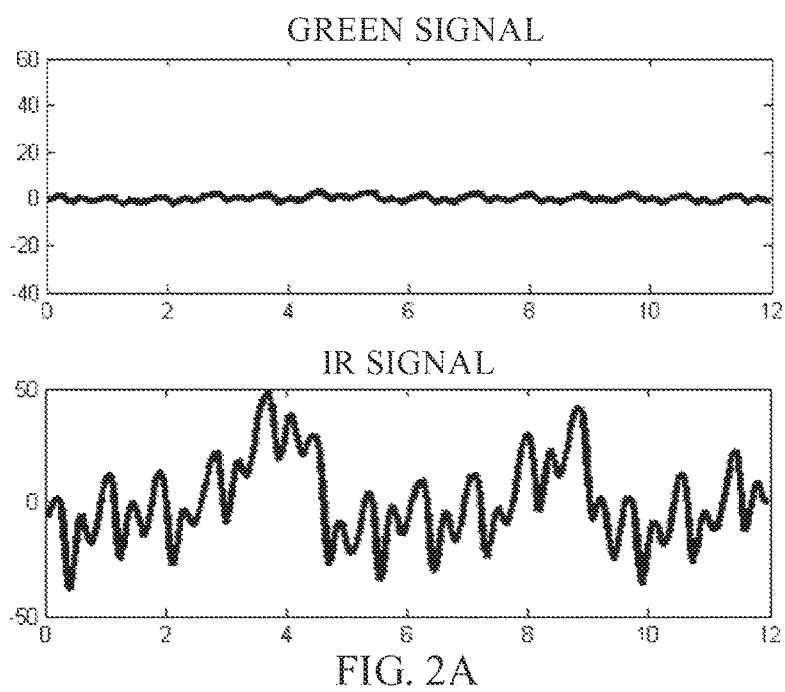
FIGS. 2A, 2B and 2C illustrate the use of green and infrared light in measuring pulse rate, for example, by using the measurement arrangement disclosed in FIG. 1A and FIG. 1B.
Figure 2B:
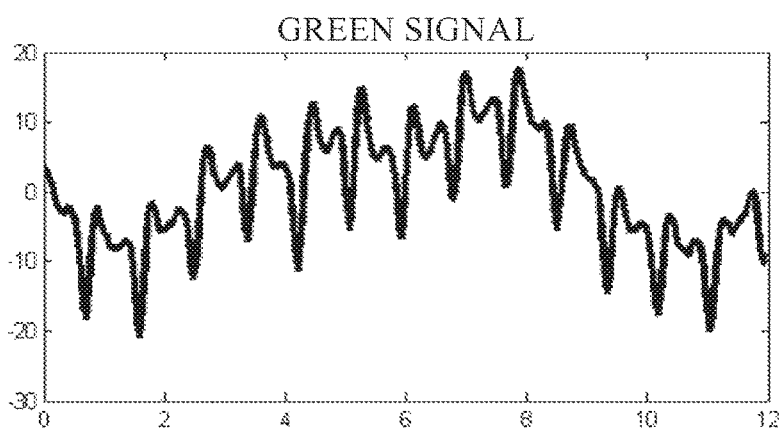
Figure 2C:
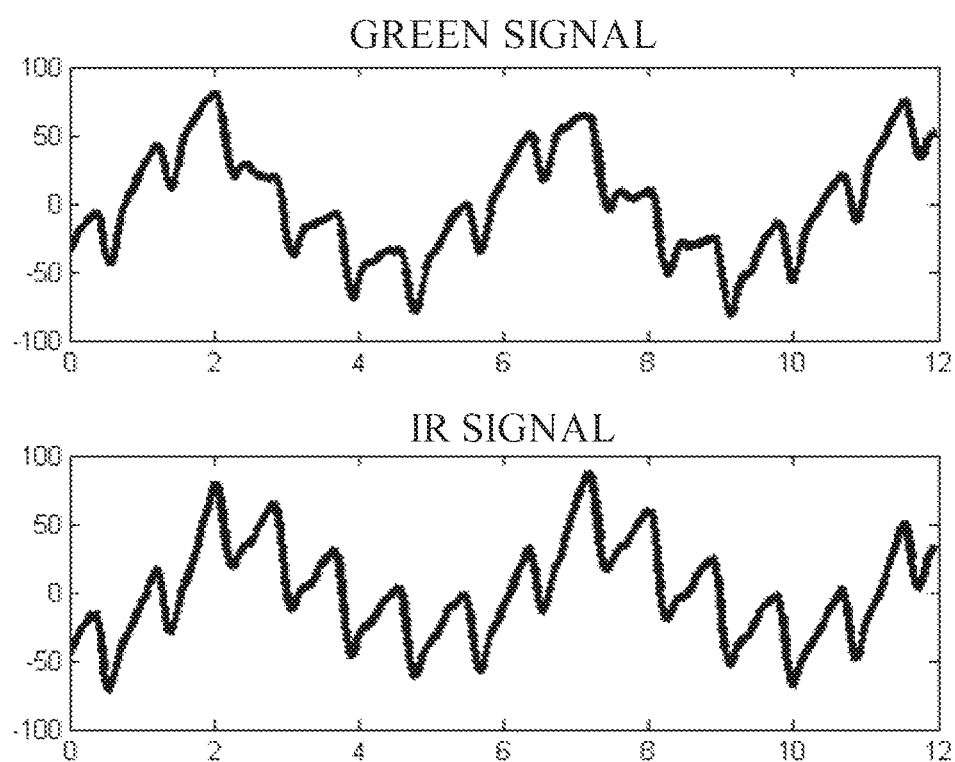

FIGS. 2A, 2B and 2C illustrate the use of green and infrared light in measuring pulse rate, for example, by using the measurement arrangement disclosed in FIG. 1A, 1B, 1C, 1D or FIG. 1E.

FIG. 2A illustrates a comparative situation between signals detected by a light detector for green light and infrared light when cold skin is measured. The horizontal axis represents time and the vertical axis detected signal amplitude. The heart rate is clearly seen in the infrared signal but is almost invisible in the green signal. In this situation use of infrared light would be preferred for reliable heart rate detection.

FIG. 2B illustrates a comparative situation between signals detected by a light detector for green light and infrared light when warm skin is measured. The horizontal axis represents time and the vertical axis detected signal amplitude. The heart rate can be seen in both signals. In such a situation use of infrared light would be preferred due to lower power consumption.

FIG. 2C illustrates a comparative situation between signals detected by a light detector for green light and infrared light when movement is present during measuring. The horizontal axis represents time and the vertical axis detected signal amplitude. It can be seen that almost no movement effect is present in the green signal but the infrared signal is disturbed by the movement. In this situation, green light would be preferred for reliable heart rate detection.

Figure 3:
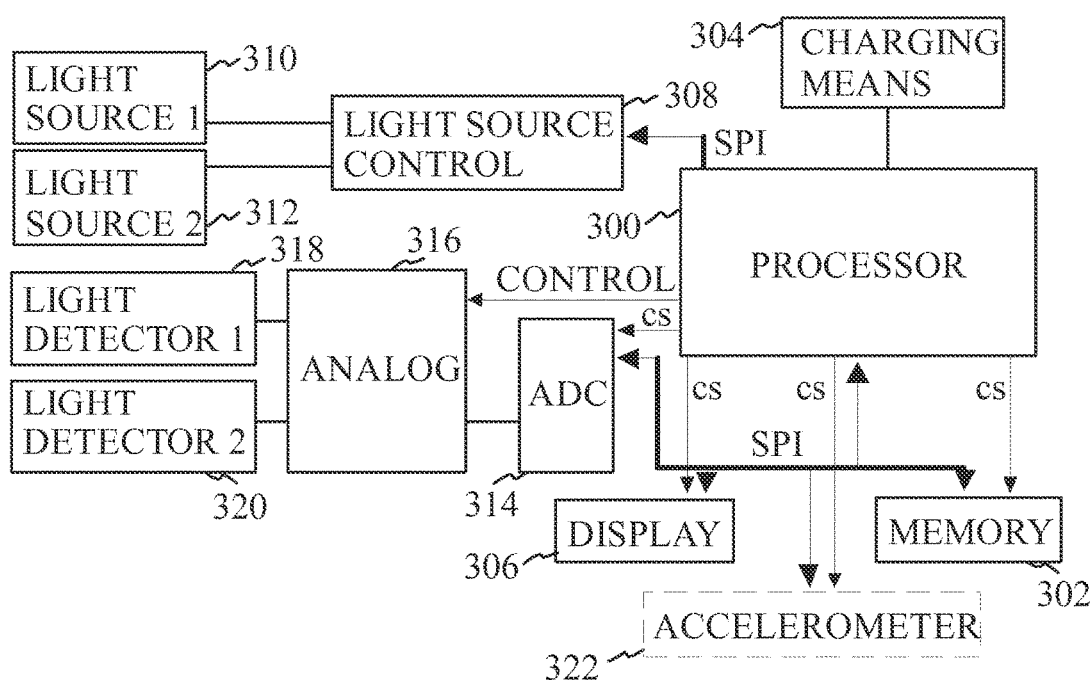
FIG. 3 is a block diagram illustrating an embodiment of a portable pulse measuring device.

FIG. 3 is a block diagram illustrating an embodiment of a portable pulse measuring device. The pulse measuring device may take a form of a wrist watch type device or any other applicable form. It should be noted that the present invention may be attached to any form and location at skin where firm skin attachment may be reached. For example, an arm or a forearm band, a waist band, a head band, or a tight band are possible embodiments for such a measurement.

The device comprises a processor 300 which is arranged to process information received via various signal paths from other elements of the device and to provide control information for the device elements. A memory 302 connected to the processor 300 is arranged to store program logic based on which the processor 300 performs various operations related to the invention. The memory 302 may also store pulse rate measurement data. The processor 300 is connected to a light source control block 308 which is arranged to control a first light source 310 and a second light source 312 based on the instructions received from the processor 300 to emit light signals towards human tissue. "SPI" in connection with some signal paths means Serial Peripheral Interface via which serial communication can be performed via various blocks. "cs" in connection with some signal paths means that together with using SPI cs can be used to point with which block to communicate. "CONTROL" in connection with a signal path between the analog block 316 and the processor 300 is a control signal having a set of control lines for controlling analog circuitry such as power on/off of the analog block 316 and data sampling timing control.

A first light detector 318 and a second light detector 320 are arranged to receive light reflected from the human tissue. The signals detected by the light detectors 318, 320 are received by an analog block 316, which may perform low pass filtering, and alternatively or additionally may perform band pass or high pass filtering to drop off unwanted signals. There could be also control mechanism to read values in (sample and hold circuit) when there is an ongoing measurement (i.e. light-emitting source on). Output of the block 316 will then be transformed to digital form by the ADC 314.

The device also comprises a display 306 which is arranged to display a heart rate reading in response to instructions from the processor 300. Charging means 304 are also provided to supply operating power to the device. The device may additionally comprise also an accelerometer or other sensor relative to movement of the device 322. Alternative embodiments to an accelerometer include for example gyroscope, magnetometer, force sensitive film between the device and the skin, or optical sensor arranged to measure tissue deformations. Signals from the movement sensor may be used in compensating unwanted movement errors in the signals detected by the light detectors 318, 320.

Although FIG. 3 discloses two light-emitting sources and two light detectors, other embodiments of the invention may comprise a lighting configuration comprising at least three elements selected from a light-emitting source and a light detector, wherein the lighting configuration comprises at least one light-emitting source and at least one light detector.

The device may also comprise components or elements not disclosed in FIG. 3, for example, at least one of a bluetooth chip, a bluetooth antenna, a data connection interface, a mechanical button or buttons, a light sensor (for example, an ambient light sensor) etc.

Figure 4:
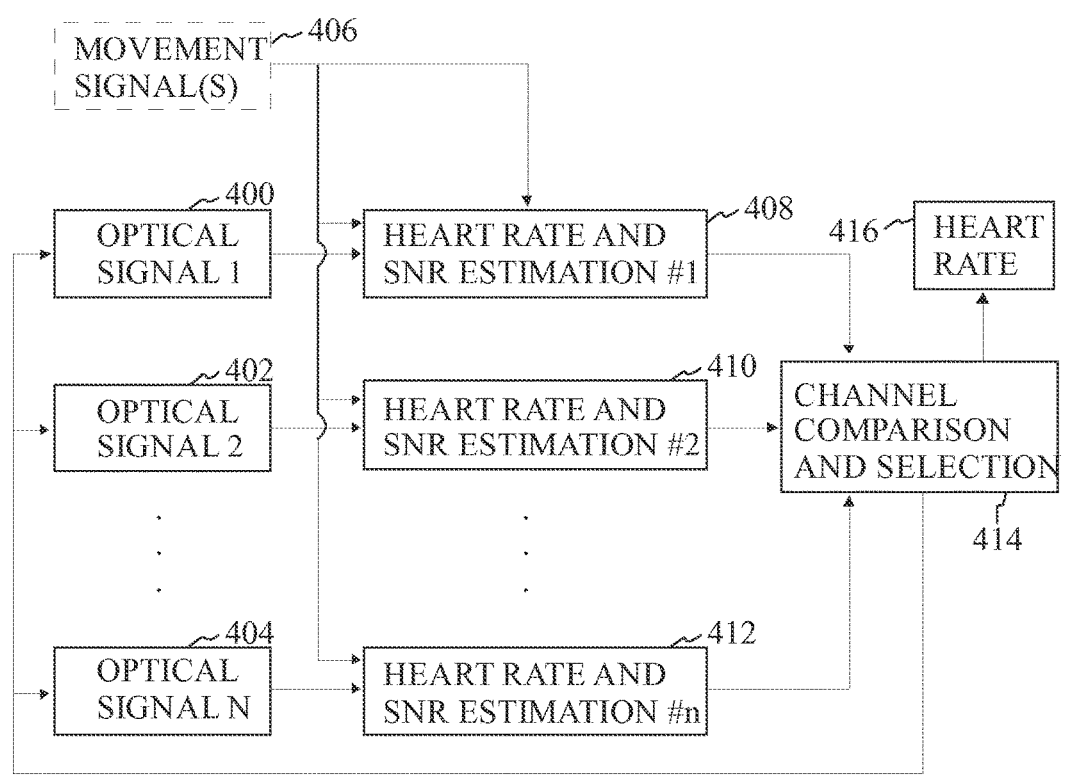
FIG. 4 is a block diagram illustrating the operating process of a pulse measuring device according to one embodiment of the invention.

FIG. 4 is a block diagram illustrating the operating process of a pulse measuring device according to one embodiment of the invention.

FIG. 4 illustrates multiple optical signals 400, 402, 404 which are provided with light detectors, for example, photo detectors. A processor receives the optical signals and processes them to determine a heart rate 408, 410, 412 based on the signals. A movement signal or signals 406 may also be provided to the processor. The movement signal is a signal related to the movement of the sensor (for example, an acceleration sensor) or movement of the tissue. For example, this may be accelerometer signal, or it may be another optical signal which is insensitive to blood flow in the tissue. The optical signals are easily distorted due to various movements and the movement signals are used to filter out movement from the optical signals.

Furthermore, tissue deformation due to movement causes major changes in light reflection paths within the tissue, leading to major changes in light intensity observed in a light detector when the tissue is illuminated with constant light intensity. This relationship is dependent on tissue volume through which the light travels, i.e. the higher the volume the more changes are caused by movements. Therefore, in an optimal solution, tissue volume to be illuminated should be minimized to minimize artifacts in the signal while still sufficiently including illumination of the tissue with active blood perfusion.

Since the pulse rate measuring device comprises at least two light-emitting sources and at least one light detector, there are multiple channels to measure pulse (depending on the amount of light-emitting sources and wavelengths used and the amount of light detectors).

As a general rule, a best possible signal at a given point of time may be selected 414 based on which the pulse rate is determined. As movement artifact is dependent on volume of the illuminated tissue the optimal selection of a deeper measurement or a smaller measurement depth) is dependent also on movement status and blood perfusion status, and individual differences.

Therefore, a reliability factor for each measured channel may be used as an estimate of the reliability of the heart rate reading (called here as SNR). As an example, the SNR may be calculated as $$SNR = \|X_{HR}\| / \|X_{nHR}\|$$

where $X_{HR}$ is the ratio of the signal related to pulsative blood flow, $X_{nHR}$ is the ratio of the signal not related to pulsatile blood flow, and $\|\cdot\|$ is the signal norm operator, for example, power, absolute power, amplitude or mean amplitude. $X_{HR}$ and $X_{nHR}$ may be adaptively estimated from the signal. It is clear to a person skilled in the art that several other possible norm operators may also be used. It is also evident that also other ways of determining the SNR may be used than the one disclosed above. Usually, the most reliable channel (i.e. having the highest SNR value) is used as a heart rate 416 estimate. In another embodiment, several channels may be combined, for example, by an averaging operation to estimate the heart rate. It is evident, that also other operations to combine information in different channels may be envisioned, such as weighted averaging or nonlinearly weighted combination.

In one embodiment, the following iteration process may be executed.

1) If the reliability factor is above a selected threshold the heart rate reliability is deemed good in a given channel and this reading may be used as heart rate output. If several reliability factors are above the threshold, the channel having the highest reliability factor may be selected. Furthermore, one or more other channels may be shut down to save battery power. Furthermore, also light intensity of the best channel may be reduced to optimize power consumption as long as the reliability factor remains above a selected threshold. In another embodiment, each light source has predetermined power consumption. The optimization may include selecting a channel the reliability factor of which exceeds the selected threshold and where the power consumption for achieving the selected threshold is at a minimum.

2) If the reliability factor is below the selected threshold, one or more channels may be powered on (if they are not active at the present moment) or their light intensity may be increased to allow change of the optimal channel if another channel and/or higher light intensity would provide better reliability factor.

3) If the reliability factor is below another selected threshold (meaning a very poor signal) then such a channel may be totally shut down to avoid spending power on a channel which does not contribute to heart rate detection.

By using the above iteration process a measurement depth is adaptively chosen to provide the most reliable heart rate to adapt the measurement depth to best match the depth where blood flow actually occurs in each individual and in each condition, taking into account the effect of tissue deformations caused by movements. This will significantly improve the reliability of the heart rate estimate in different conditions (for example, in cold/warm skin situation, at rest condition, in an intensive training situation etc.) and between different individuals. Furthermore, active measurement channel or channels and their light intensities may be adaptively chosen to optimize the reliability factor. This will also save battery power.

Table 1 represents general principles for selecting the optimal light-emitting source-light detector combination.

TABLE 1

|  |  | Movement | |
|---|---|---|---|
|  |  | Low | High |
| Blood perfusion (temperature) | Low | IR and large d | IR and small d<br>Green and large d |
|  | High | IR and small d | Green and small d |

When "IR and large d" is applied, low power is needed and deep penetration is achieved. When "IR and small d" is applied, lower power level is achieved than with green light. When "IR and small d" is applied, low power and deeper penetration than with green light is achieved. When "Green and large d" is applied, the configuration is less sensitive to movement artefacts than the infrared light. When "Green and small d" is applied, the configuration is the most insensitive to movement artefacts and suitable for measurement, for example, during intensive sports.

Figure 5:
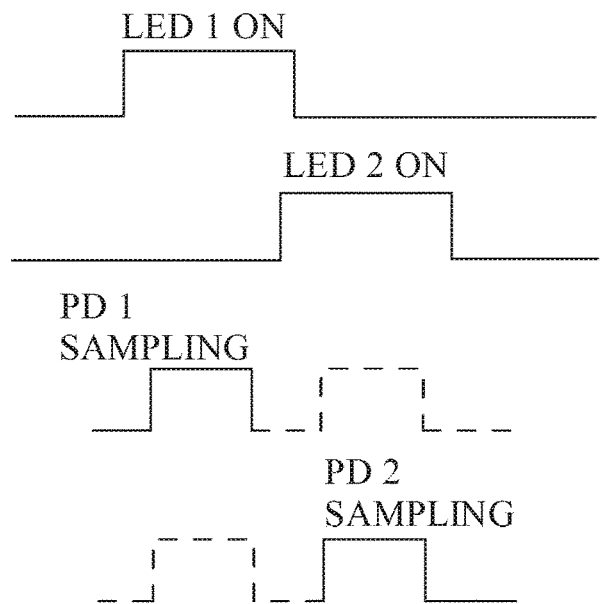
FIG. 5 illustrates channel logic when a pulse measuring device comprises two light-emitting sources and two light detectors according to one embodiment of the invention.

FIG. 5 illustrates channel sampling logic when a pulse measuring device comprises two light-emitting sources and two light detectors according to one embodiment of the invention.

The sampling frequency is, for example, 85.3 Hz at the sample-and-hold circuit for the all channels. The general sampling sequence is LED on—sampling—LED off. When more than one led color is used per measurement, it is important to phase the measurements off from each other.

Thus, an exemplary sampling logic may be: LED1 on—sampling—LED1 off—LED2 on—sampling—LED2 off as indicated by FIG. 5.

An AD converter is sampling at 21.3 Hz. There may be a low pass filter at each channel at the front of AD converter. When having two photo detectors and two different color LEDs the total amount of measurement channels is four. Since the configuration has two receiving channels, it is possible to get two sets of data for monitoring and analyzing at a time. The analyzing period may be set to a predetermined value and after each analyzing period, another measurement channel to be monitored and analyzed may be selected.

One possible state diagram comprises four sampling states. An AD conversion will be initiated for channel 1 at state 1 and for channel 2 at state 2. The third may be a "rest" state doing nothing for the measurement. The fourth state can be used to collect movement data, for example, from a movement sensitive sensor.

In this example, there are four optical channel combinations for actual measurements. The device may keep in memory the optical channel combination used. Changing the optical channel combination selection may be done after data has been analyzed. Each optical channel combination may also have a LED power value stored in the memory. This value may be also tuned after data has been analyzed. The analysis may be performed in blocks, for example every 6 seconds, or over a sliding window of a certain duration, for example, 6 seconds.

The channel sampling logic illustrated in FIG. 5 may also be used in other configurations where there are at least two light-emitting sources and at least one light detector. Further, in one embodiment, more than one light detector may be simultaneously used to sample a single light-emitting source.

Figure 6:
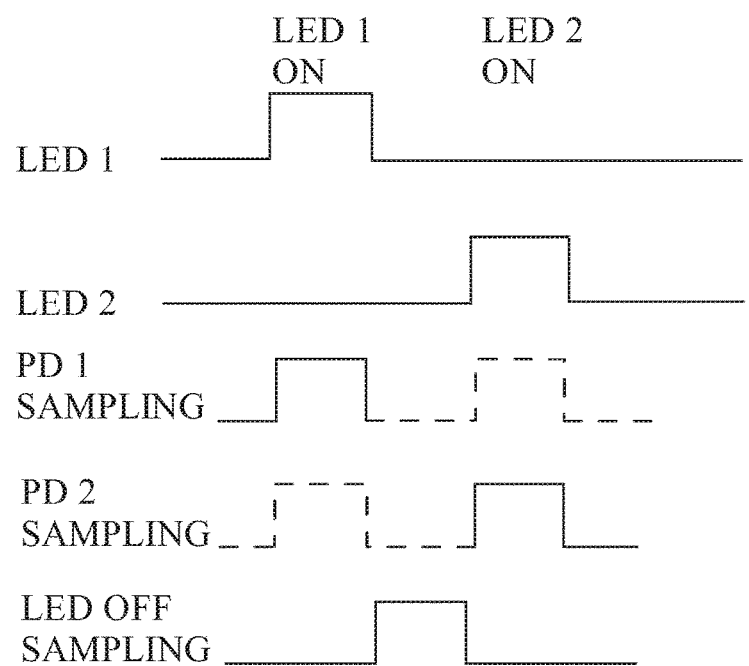
FIG. 6 illustrates channel logic when a pulse measuring device comprises two light-emitting sources and two light detectors according to another embodiment of the invention.

FIG. 6 illustrates channel logic when a pulse measuring device comprises two light-emitting sources and two light detectors according to another embodiment of the invention. The embodiment in FIG. 6 is similar with the embodiment of FIG. 5 with the exception that another sampling period has been introduced. When LED 1 has been switched off and before LED is switched on, there exists an additional sampling period ("LED off sampling"). This sampling may be performed with one or more light detectors (i.e. photo detectors).

The measurements in the LED off state (i.e. a measuring an interference signal) may be used to reduce interference when performing measurements in the LED on state. Reduction of the interference may be done, for example, by adaptive filtering where LED off state signal is used as an estimate of the signal noise, and an adaptive filter is used to calculate an estimate of the impact of noise on LED on state signal, and a cleaned signal is achieved by a subtraction operation of these two. There are several possibilities known to the skilled person to implement such an adaptive filter and its adaptation.

The channel sampling logic illustrated in FIG. 6 may also be used in other configurations where there are at least two light-emitting sources and at least one light detector. Further, in one embodiment, more than one light detector may be simultaneously used to sample a single light-emitting source.

It is obvious to a person skilled in the art that with the advancement of technology, the basic idea of the invention may be implemented in various ways. The invention and its embodiments are thus not limited to the examples described above, instead they may vary within the scope of the claims.

The invention claimed is:

1. A portable pulse measuring device, comprising:
a lighting configuration comprising at least two light-emitting sources for emitting radiant energy through a human body tissue and two light detectors for detecting the intensity of said radiant energy from the two light-emitting sources after propagation through the human body tissue and for providing input signals representative of said propagation, wherein the at least two light-emitting sources comprise a first light-emitting source emitting green or blue light and a second light-emitting source emitting red or infrared light for determining pulse rate; and
processing means configured to determine pulse rate in response to processing the input signals;
wherein elements in the lighting configuration are arranged in the portable pulse measuring device in a configuration where a first light detector and a second light detector and the first light-emitting source are disposed substantially along a first axis, the first light-emitting source being disposed between the first and second light detectors, and the first light-emitting source and the second light-emitting source are disposed along a second axis differing from the first axis and wherein the distances from the first light-emitting source to the two light detectors differ from each other and the distances from the second light-emitting source to the two light detectors differ from each other; and
wherein wavelengths of the at least two light-emitting sources and the distances from the first light-emitting source to the two light detectors and the distances from the second light-emitting source to the two light detectors have been chosen to enable measurement of a variety of measurement depths in the human body tissue, providing sensitivity to blood flow, and insensitivity against to movement artefacts in varying conditions.

2. The device according to claim 1, wherein the first light-emitting source emits green light and the second light-emitting source emits infrared light, wherein distance between the center of the first light detector and the first light-emitting source is between 2.0 mm and 4.0 mm, the distance between the center of the second light detector and the first light-emitting source is between 4.0 mm and 6.0 mm the distance between the center of the first light detector and the second light-emitting source is between 4.0 mm and 6.0 mm, and the distance between the center of the second light detector and the second light-emitting source is between 6.5 mm and 8.5 mm.

3. The device according to claim 1, further comprising blocking means for blocking direct light leakage from the light-emitting sources to the light detectors.

4. The device according to claim 1, wherein the processing means is configured to:
determine whether a channel comprising a specific light detector detecting radiant energy from a specific light-emitting source exceeds a first reliability factor threshold, the reliability factor indicating an estimate of the reliability of the heart rate reading for the channel; and
select a channel having a reliability factor above the first reliability factor threshold.

5. The device according to claim 4, wherein the processing means is configured to:
select a channel having the highest reliability factor.

6. The device according to claim 4, wherein the processing means is configured to:
select a channel having the lowest power consumption.

7. The device according to claim 4, wherein the processing means is configured to:
shut operating power from at least one channel not selected.

8. The device according to claim 4, wherein the processing means is configured to:
reduce light intensity of the light-emitting source of the selected channel so that the reliability factor of the selected channel exceeds the first reliability factor threshold.

9. The device according to claim 4, wherein the processing means is configured to:
increase light intensity of the light emitting source of the selected channel so that the reliability factor of the selected channel exceeds the first reliability factor threshold.

10. The device according to claim 7, wherein the processing means is configured to:
determine that the reliability factor of a channel is below the first reliability factor threshold;
power on at least one channel the operating power of which was earlier shut down;
determine the reliability factor again for one or more channels; and
reselect a channel having the reliability factor above the first reliability factor threshold, or having the reliability factor above the first reliability factor threshold and the lowest power consumption.

11. The device according to claim 4, wherein the processing means is configured to:
determine that the reliability factor of a channel is below a second reliability factor threshold; and
shut down operating power from the channel.

12. The device according to claim 4, wherein the reliability factor is calculated as $$SNR = \|X_{HR}\|/\|X_{nHR}\|$$

where $X_{HR}$ is the portion of the signal related to pulsative blood flow, $X_{nHR}$ is the portion of the signal not related to pulsatile blood flow, and $\|\cdot\|$ is a signal norm operator.

13. A portable pulse measuring device, comprising:
a lighting configuration comprising at least two light-emitting sources for emitting radiant energy through a human body tissue and at least one light detector for detecting the intensity of said radiant energy after propagation through the human body tissue and for providing input signals representative of said propagation, wherein the at least two light-emitting sources comprise a first light-emitting source emitting green light and a second light-emitting source emitting infra-red light for determining pulse rate;
processing means configured to determine pulse rate in response to processing the input signals;
wherein the elements in the lighting configuration are arranged in the portable pulse measuring device in a configuration where the distance from the first light-emitting source to a first light detector and the distance from the second light-emitting source to the first light detector differ from each other and wherein the distance between the center of the first light detector and the first light-emitting source is between 2.5 mm and 4.5 mm, and the distance between the center of the first light detector and the second light-emitting source is between 4.0 mm and 7.0 mm;
wherein wavelengths of the first and second light-emitting sources and the distance between the center of the first light detector and the first light-emitting source and the distance between the center of the first light detector and the second light-emitting source have been chosen to enable measurement of a variety of measurement depths in the human body tissue and providing sensitivity to blood flow and insensitivity against to movement artefacts in varying conditions.

14. The portable pulse measuring device according to claim 13, wherein the distance between the center of the first light detector and the first light-emitting source is about 3.6 mm.

15. The portable pulse measuring device according to claim 13, wherein the distance between the center of the first light detector and the second light-emitting source is about 6.0 mm.

16. The portable pulse measuring device according to claim 14, wherein the distance between the center of the first light detector and the second light-emitting source is about 6.0 mm.

* * * * *